United States Patent [19]

Shervington et al.

[11] Patent Number: 5,954,232
[45] Date of Patent: *Sep. 21, 1999

[54] GAS DELIVERY SYSTEM

[75] Inventors: Evelyn A. Shervington, Nr. Petersfield; David W. Birch, Bordon, both of United Kingdom

[73] Assignee: The BOC Group plc, Windlesham, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/691,901

[22] Filed: Aug. 1, 1996

[30] Foreign Application Priority Data

Aug. 2, 1995 [GB] United Kingdom ............... 95 15825
Apr. 16, 1996 [GB] United Kingdom ............... 96 07877

[51] Int. Cl.$^6$ ........................................ A61M 5/30
[52] U.S. Cl. ............................ 222/4; 222/3; 222/637; 222/541.6; 215/49; 215/253; 220/266; 604/70; 604/200
[58] Field of Search ............... 604/63, 70, 200; 215/47, 48, 49, 250, 253, 255; 220/265, 266, 269, 270; 206/222, 363, 364; 222/3, 4, 153.07, 153.06, 637, 541.6, 541.9

[56] References Cited

U.S. PATENT DOCUMENTS

| 3,088,680 | 5/1963 | Fulton et al. ............... 222/541.6 X |
| 3,788,315 | 1/1974 | Laurens . |
| 3,853,125 | 12/1974 | Clark et al. ............... 604/70 |
| 4,248,227 | 2/1981 | Thomas ............... 222/541.9 X |
| 4,780,100 | 10/1988 | Moll ............... 222/635 X |
| 4,913,699 | 4/1990 | Parsons ............... 604/70 X |
| 5,009,637 | 4/1991 | Newman et al. ............... 604/70 X |
| 5,143,288 | 9/1992 | Kohler et al. ............... 222/402.18 X |
| 5,314,097 | 5/1994 | Smrt et al. ............... 222/394 X |

FOREIGN PATENT DOCUMENTS

| 1382399 | 11/1964 | France ............... 604/200 |
| 253744 | 6/1926 | United Kingdom . |
| 2 060 154 | 4/1981 | United Kingdom . |
| 94/24263 | 10/1994 | WIPO . |

*Primary Examiner*—Kenneth Bomberg
*Attorney, Agent, or Firm*—Philip H. Von Neida; Salvatore P. Pace

[57] ABSTRACT

A gas delivery system includes a capsule for storing a propellant fluid, e.g. helium under pressure, e.g. between about 60 and 80 bar. The capsule is provided with a stopper having a stem formed with a frangible section. In use, mechanical means is employed to rupture the stem about the frangible section to release the fluid under high pressure.

2 Claims, 3 Drawing Sheets

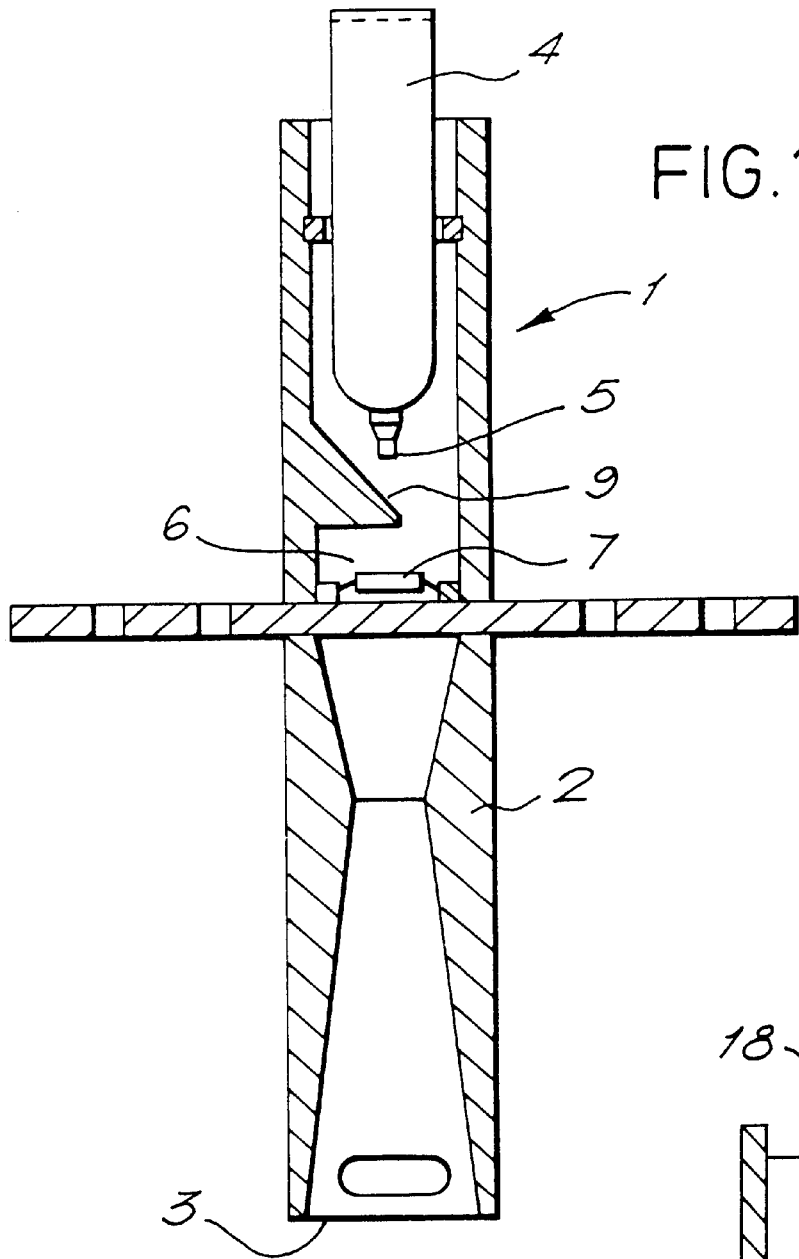
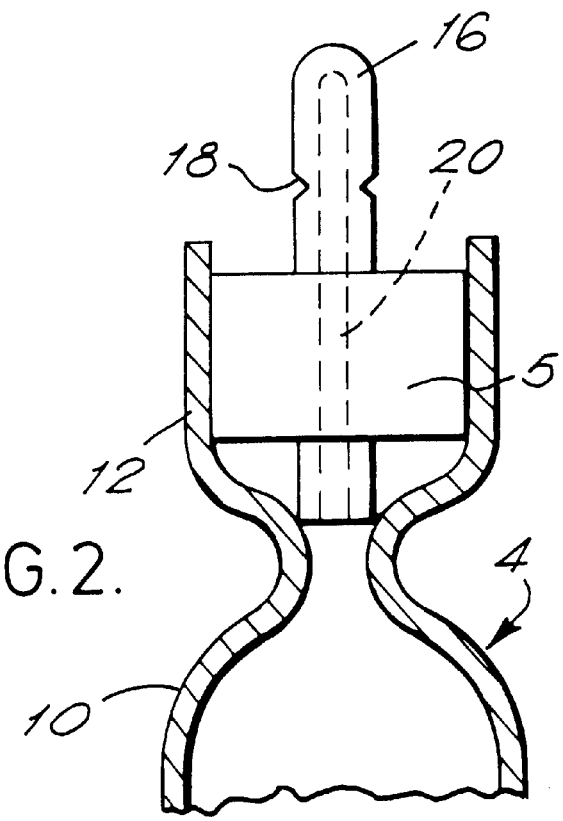
FIG.1.
FIG.2.

GAS DELIVERY SYSTEM

The present invention relates to gas delivery systems and in particular to capsules for containing small volumes of fluid at high pressure, that is, between 60 and 80 bar for use in such systems.

BACKGROUND OF THE INVENTION

The use of sealed capsules is well known in circumstances where the force of the fluid under pressure is employed to dispense a substance such as discharging draught beer from a beer dispenser or expelling soda water from a soda siphon.

It is also known to employ sealed capsules containing helium at high pressures, in the order of 30–40 bar, in medical devices using the energy of the pressurized helium to drive a therapeutic agent through the skin of a patient.

In PCT published application WO94/24263 there is described a needleless syringe, which includes a metal capsule containing helium gas at high pressure which is used to force particles of a therapeutic agent through the skin of a patient in a substantially painless manner. The capsule is detachable from the remainder of the syringe and once used, either a new charge of gas can be placed in the capsule or more favorably, the capsule can be discarded and a new capsule charged with gas can be attached to the remainder of the syringe.

In the circumstance where the gas capsule is a throw away item, it is important that it can be manufactured simply and cheaply. In medical applications, helium gas is a favored fluid since it is very light which makes it suitable for use as a propellant for therapeutic agents in that when it impinges against the skin of a patient it will bounce off into the atmosphere and not pass through. However, helium can be disadvantageous in that, because it is light, it is difficult to contain since it will leak through the most minuscule fault in a container.

Furthermore, in medical applications it is important that the helium gas can be released from the gas capsule with the minimum of force by the user, for example, finger force.

UK Patent 253744 describes a metal capsule for gases or liquids under pressure which can be used to inflate a flexible container. The capsule comprises a cylindrical hollow body having a neck portion formed with an internal thread. A closure member has a corresponding external thread and is screwed into the neck portion.

The closure member has an outwardly projecting stem which is hollowed so that it may easily be broken. The stem has an external thread for connection to a handle forming part of the flexible container. When it is required to liberate the gases or liquids in the capsule, the hollow body is moved laterally relative to the handle and the stem connected thereto such that the stem is ruptured thereby releasing the gas from the interior of the hollow body.

Such a capsule, however, is not effective for containing a very light gas such as helium for a reasonable length of time at pressures in the order of 60 to 80 bar since the helium molecules will leak through the helical path between the co-operating internal thread of the neck portion and external thread on the closure member. Furthermore, in order to break the stem a considerable laterally force needs to be applied, that is, a force greater than finger pressure having no mechanical advantage. A further disadvantage is that the capsule is expensive to manufacture in that screw threads have to be turned on both the neck portion and the closure member.

In accordance with the present invention, a gas delivery system is provided which avoids the disadvantages of the prior art systems. The gas delivery system of the invention contains a capsule for fluid under high pressure which can be manufactured simply and cheaply and which is substantially leakproof even when the fluid under pressure is helium. the capsules of the invention are further advantageous in that they can be opened with finger pressure having no or relatively very little mechanical advantage without causing the gas delivery device of which it forms a part, to move when held in one hand.

BRIEF SUMMARY OF THE INVENTION

According to the present invention, a gas delivery system comprises a capsule for storing a fluid under pressure, the capsule having a hollow body with a neck, a stopper located in the neck in a fluid tight manner, the stopper having a stem extending outwardly from the neck and including a frangible section, the stopper also having a passage in communication at one end with the interior of the hollow body which extends at least to the frangible section and mechanical means for rupturing the frangible section thereby allowing the escape of the fluid through the passage from the hollow body.

BRIEF SUMMARY OF THE DRAWINGS

The following drawings are illustrative of embodiments of the invention and are not intended to limit the invention as encompassed by the claims forming part of the application.

FIG. 1 is a diagrammatic sketch of a needle-less medical device including a gas delivery system of the present invention;

FIG. 2 is a side view of a hollow neck of a first capsule for storing a fluid under pressure;

DETAILED DESCRIPTION OF THE PREFERRED EMBODIMENTS

Figure 3:
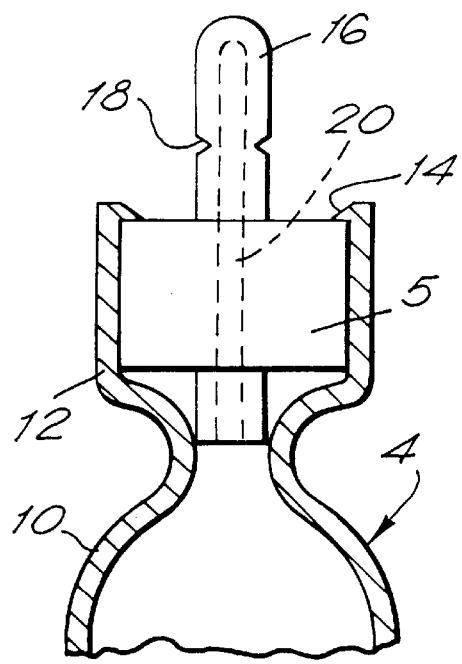
FIG. 3 is a view similar to FIG. 2 of a second embodiment of capsule for containing a fluid under pressure.

The system according to the present invention comprises a capsule for storing fluids under pressure having a hollow body with a neck having a stopper therein in fluid tight manner. The stopper may be maintained within the hollow neck by crimping the free end of the hollow neck over a shoulder formed on the stopper, but preferably is laser welded within the neck . Laser welding is utilized since glue or conventional welding could contaminate a medical grade gas contained in the capsule.

The stopper has a stem which extends outwardly from the neck and includes a frangible section. The stopper also contains a passage in communication at one end with the interior of the hollow body which extends at least to the frangible section and mechanical means for rupturing the frangible section thereby allowing the escape of the fluid through the passage from the hollow body. In one embodiment of the invention, the stem may be formed at a right angle with a major portion of the stem above the frangible portion at substantially right angles to the hollow neck.

Embodiments of the invention will now be described, by way of example, with reference to the FIGS. of the accompanying diagrammatic drawings. As shown in FIG. 1, a needle-less medical device is in the form of a needle-less syringe 1 which comprises essentially a casing 2 in the form of an elongate hollow tube open at a distal end to define an outlet 3. The casing 2 contains a gas capsule 4 for storing a fluid 42, for example, helium under high pressure, that is between 60 and 80 bar. An inclined surface 9 is formed on the interior of the surface of the casing 2 spaced from but adjacent to the stopper 5 of the gas capsule 4. The gas capsule 4 is so mounted within the casing 2 that when finger pressure is applied to the proximal end of the gas capsule 4, the capsule will move downwardly (as shown) until the stopper 5 strikes the surface 9. Within the casing 2 adjacent the stopper 5 of the gas capsule 4 there is formed a chamber 6 for receiving a powdered agent, for example, a drug 7.

Referring also to FIG. 2, the gas capsule 4 comprises a hollow body 10 with a hollow neck 12 extending therefrom. The stopper 5 is located within the neck 12 in a fluid tight manner. In this embodiment, the stopper 5 is laser welded within the hollow neck 12, forming a weld 40. The stopper 5 includes a stem 16 extending outwardly from the hollow neck and including a frangible section 18. The stopper 5 also has formed therein a passage 20 which communicates at one end with the interior of the hollow body 10 and extends past the frangible section 18 to terminate in a blind hole.

In use, when it is desired to treat a patient by means of the syringe 1, the drug 7 is placed in the chamber 6 and the outlet 3 is placed against the skin of the patient. Finger pressure is applied to the proximal (upper as shown) end of the gas capsule 4 which causes the capsule 4 to move downwardly until the stem 16 engages the inclined surface 9 thereby rupturing about the frangible section 18 with the subsequent release of the contained fluid. The released fluid passes out from the capsule 4 into the chamber 6 where it entrains the powdered drug 7. The fluid with the entrained powdered drug 7 then passes through the outlet 3 with the drug passing through the skin of the patient whereas the molecules of fluid, when it is helium, bounce off the skin into the atmosphere.

In the embodiment of gas capsule 4 illustrated in FIG. 3, the structure is substantially the same as with the capsule 4 illustrated in FIG. 2 with the exception that the free end 14 of the hollow neck 12 is crimped about a shoulder of the stopper 5 to maintain the stopper in a gas tight manner within the hollow neck 12.

Referring now to FIG. 4, again the stopper 5 is substantially as described with reference to FIGS. 2 and 3, however the stem 16 is configured such that a major part beyond the frangible section 18 is at right angles to the remainder of the stem. This configuration is of particular utility when, instead of a inclined surface 9, as illustrated in FIG. 1, a simple abutment is used to exert a force adjacent the free end of the stem 6 to rupture the frangible section 18.

Figure 4:
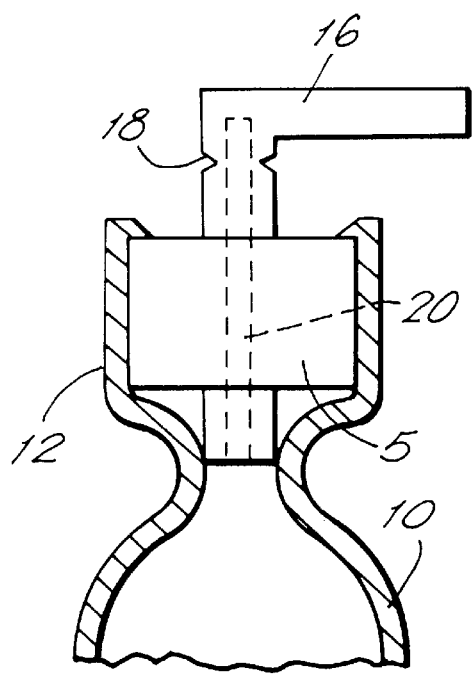
FIG. 4 is a view similar to FIGS. 2 and 3 of yet a further embodiment of a gas capsule for containing a fluid under pressure.
Figure 5:
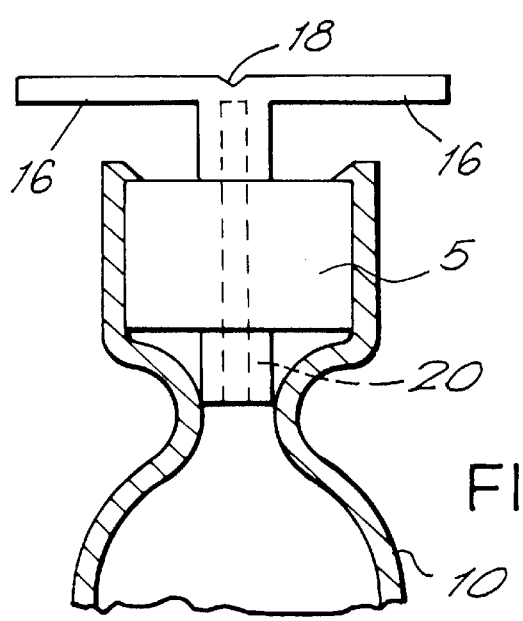
FIG. 5 is yet a further view similar to FIGS. 2, 3 and 4 of yet a further embodiment of a capsule for containing a fluid under pressure.

The embodiment illustrated in FIG. 5 is very similar to that illustrated in FIG. 4 except that the stem 16 terminates in two parts each at right angles to the remainder of the stem with the frangible section 18 immediately above the blind end of the passage 20.

Figure 6:
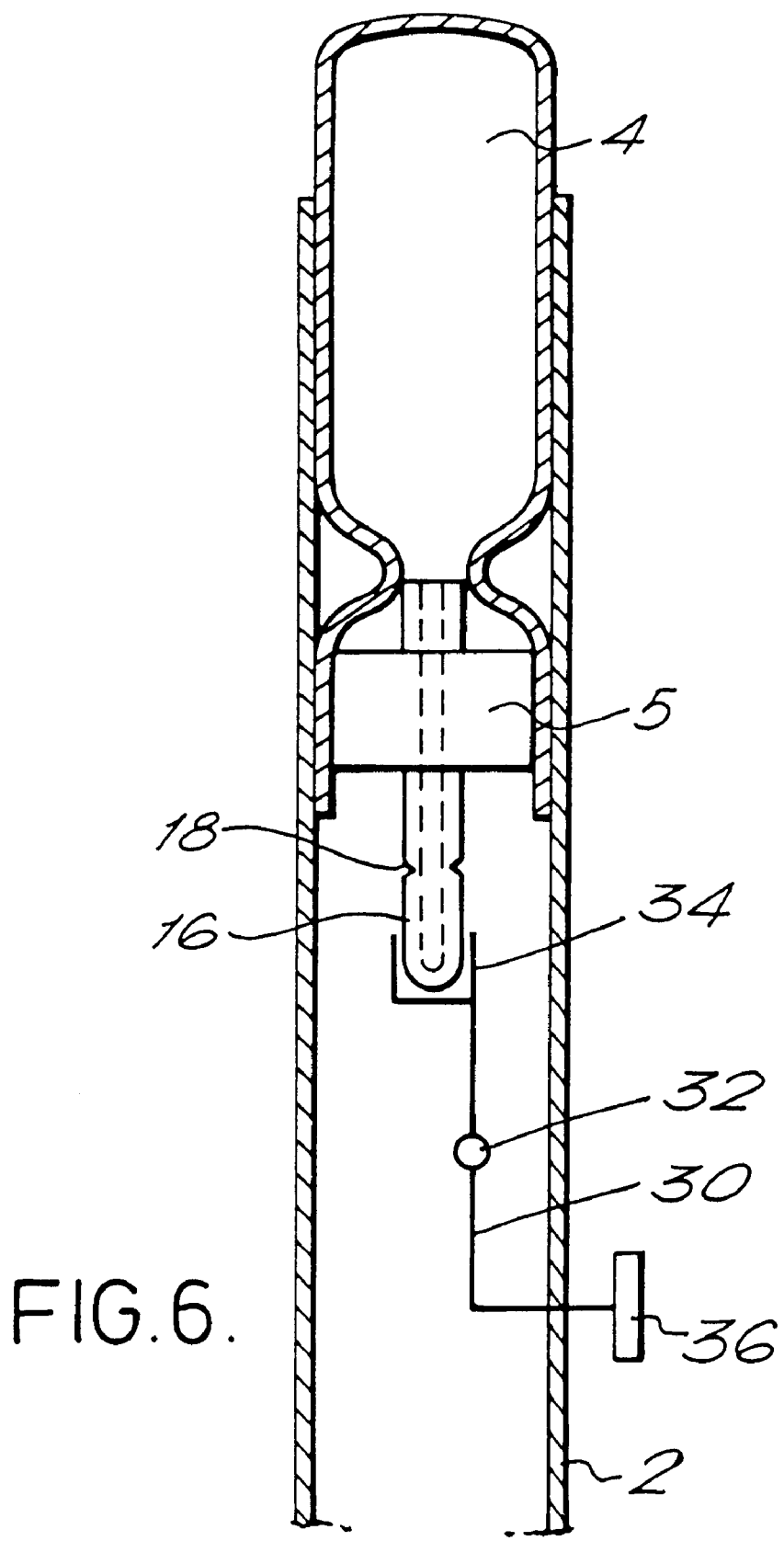
FIG. 6 is a diagrammatic sketch similar to FIG. 1 but showing a different mechanical means for rupturing a gas capsule.

Referring now to FIG. 6, this illustrates the upper portion of a needle-less syringe similar to that illustrated in FIG. 1 but in which the stem 16 of the stopper 5 is caused to rupture about the frangible section 18 by means of a mechanical push button lever device.

The lever device includes an arm 30 mounted for pivotal movement about a pivot point 32. One end of arm 30 is formed with a cup-shaped member 34 which embraces the free end of the stem 16. The portion of the arm 30 below (as shown) the pivot point 32 is formed through 90° and terminates in a push-button 36 located outside the casing 2 of the needle-less syringe.

In use, finger pressure on the push-button 36 will cause the cup-shaped member 34 to pivot in a clockwise sense about the pivot point 32 and thereby rupture the stem 16 about the frangible section 18.

This embodiment ensures that when the stem 16 is ruptured about the frangible section 18, the free end of the stem which separates from the remainder of the stem cannot be propelled towards the patient but is held captive by the cup-shaped member 34.

The capsules 4 may be made from aluminium or an aluminium alloy and, if necessary may be reinforced with an outer layer of a different material 46 which could be in the form of a lattice wound tightly around a substantial part of the hollow body 10.

Furthermore, the hollow body 10 on its interior surface, which may not be impervious to a light fluid such as helium, can be provided with a layer of flexible material 44 (FIG. 5), such as aluminium foil, over a major portion of its surface which is impervious to helium and effectively blocks the flow of gas from the hollow body 10 into the passage 20 in the stopper 5.

With this modification, after the frangible section 18 is ruptured, a spike extends through the passage 20 to rupture the flexible material in order to enable the helium under pressure to exit from the hollow body 10.

It will be appreciated that all the capsules described with reference to the above embodiments are relatively inexpensive to manufacture and furthermore are relatively leak proof but easy to open.

Although reference has been made to use of the capsules 4 with a needle-less syringe for medical purposes, there are a number of other applications where the force of the contained fluid can be utilised. For example, in the inflation of balloons bearing fluorescent markings for identification by radar and for the inflation of life jackets dinghies.

We claim:

1. A system for delivering a powdered drug to the skin of a patient for medical purposes, the system comprising a capsule containing helium under pressure, the capsule having a hollow body with a neck extending therefrom, a stopper connected to the neck in a helium tight manner, the stopper having a stern extending outwardly from the neck and including a frangible section, the stopper also having a passage in communication with the interior of the hollow body which extends at least to the frangible section, a chamber for receiving the powered drug, an outlet for the powdered drug entrained in helium, and mechanical means for rupturing the frangible section thereby allowing the escape of the helium from the hollow body through the passage into the chamber to entrain the powdered drug and pass through the outlet toward the skin of the patient.

2. A powdered drug delivery system as in claim 1 further including helium stored in the capsule at a pressure between 60 and 8 bar.

* * * * *